US012778417B2

(12) United States Patent
Gonzalez et al.

(10) Patent No.: US 12,778,417 B2
(45) Date of Patent: Nov. 3, 2026

(54) IRIS REGISTRATION METHOD IN CATARACT SURGERY FOR ASTIGMATIC MANAGEMENT

(71) Applicant: AMO Development, LLC, Irvine, CA (US)

(72) Inventors: Javier Gonzalez, Palo Alto, CA (US); Michael Campos, Fremont, CA (US); Jayesh Shah, Sunnyvale, CA (US); Harvey Liu, Fremont, CA (US)

(73) Assignee: AMO Development, LLC, Irvine, CA (US)

( * ) Notice: Subject to any disclaimer, the term of this patent is extended or adjusted under 35 U.S.C. 154(b) by 191 days.

(21) Appl. No.: 18/908,636

(22) Filed: Oct. 7, 2024

(65) Prior Publication Data

US 2025/0113996 A1 Apr. 10, 2025

Related U.S. Application Data

(60) Provisional application No. 63/588,755, filed on Oct. 8, 2023.

(51) Int. Cl.
*A61B 3/103* (2006.01)
*A61F 9/008* (2006.01)
(Continued)

(52) U.S. Cl.
CPC ............ *A61B 3/1035* (2013.01); *A61F 9/008* (2013.01); *G06T 3/14* (2024.01); *G06T 7/0014* (2013.01);
(Continued)

(58) Field of Classification Search
None
See application file for complete search history.

(56) References Cited

U.S. PATENT DOCUMENTS 5,291,560 A 3/1994 Daugman
11,090,190 B2 * 8/2021 Morley .................. A61F 9/008
(Continued)

FOREIGN PATENT DOCUMENTS

DE 102020123728 A1 3/2022

OTHER PUBLICATIONS

D Morley et al., "Computing Cyclotorsion in Refractive Cataract Surgery" IEEE Transactions on Biomedical Engineering, vol. 63, No. 10, Oct. 2016 (Year: 2016).*
(Continued)

*Primary Examiner* — Soo Shin

(57) ABSTRACT

A method implemented in an ophthalmic laser system to perform iris registration based on two iris images taken with the patient at upright and supine positions, respectively. For each iris image, the iris region is transformed into a rectangular rubbersheet, with the radial and angular coordinates of the iris image respectively mapped to vertical and horizontal coordinates of the rubbersheet. A horizontal one-dimensional log-Gabor transform is applied to the rubbersheet line-by-line. The transformed rubbersheet is binarized line-by-line. The two binary rubbersheets are compared at a series of relative horizontal shifts to determine the horizontal shift value that produces the lowest Hamming distance between the two binary rubbersheets, and the cyclotorsion rotation of the eye between the upright and supine positions is calculated accordingly. Then, while the patient is in the supine position, the laser system treats the eye based on measured astigmatism axis orientation and the calculated cyclotorsion rotation.

20 Claims, 15 Drawing Sheets

(51) Int. Cl.
*G06T 3/14* (2024.01)
*G06T 7/00* (2017.01)
*G06T 7/155* (2017.01)
*G06V 40/18* (2022.01)

(52) U.S. Cl.
CPC ............ *G06T 7/155* (2017.01); *G06V 40/193* (2022.01); *A61F 2009/00887* (2013.01); *G06T 2207/30041* (2013.01)

(56) References Cited

U.S. PATENT DOCUMENTS

| | | | | |
|---|---|---|---|---|
| 2004/0263785 | A1* | 12/2004 | Chernyak | A61B 3/0025 351/205 |
| 2005/0278004 | A1* | 12/2005 | Steinert | A61B 3/113 607/89 |
| 2008/0159600 | A1 | 7/2008 | Cho | |
| 2009/0225165 | A1* | 9/2009 | Reneker | G01C 11/02 348/E7.085 |
| 2010/0110374 | A1* | 5/2010 | Raguin | A61B 3/1216 382/117 |
| 2020/0364441 | A1* | 11/2020 | O'Sullivan | G06V 40/193 |
| 2022/0142816 | A1 | 5/2022 | Morley | |
| 2022/0273493 | A1* | 9/2022 | Srinivasan | A61F 9/00825 |
| 2023/0196577 | A1* | 6/2023 | Müller | A61F 9/008 606/4 |
| 2025/0113996 | A1* | 4/2025 | Gonzalez | G06V 10/44 |

OTHER PUBLICATIONS

Bowyer et al., "Image Understanding for Iris Biometrics: A Survey", Computer Vision and Image Understanding, vol. 110, No. 02, pp. 281-307, May 1, 2008.
Daugman, John G., "High Confidence Visual Recognition of Persons by a Test of Statistical Independence", IEEE Transactions on Pattern Analysis and Machine Intelligence, vol. 15, No. 11, pp. 1148-1161, Nov. 1, 1993.
Morley et al., "Computing Cyclotorsion in Refractive Cataract Surgery", IEEE Transactions on Biomedical Engineering, vol. 63, No. 10, pp. 2155-2168, Oct. 1, 2016.

* cited by examiner

IRIS REGISTRATION METHOD IN CATARACT SURGERY FOR ASTIGMATIC MANAGEMENT

CROSS-REFERENCE TO RELATED APPLICATIONS

This application claims priority to U.S. Provisional Application No. 63/588,755, filed Oct. 8, 2023, the entire contents of which are hereby incorporated by reference in its entirety.

BACKGROUND OF THE INVENTION

This invention relates to laser-assisted ophthalmic surgeries, and in particular, it relates to a method of treating astigmatism, for example, during cataract surgery.

Astigmatism can be surgically treated by corneal curvature correction or by crystalline lens replacement with a toric intraocular lens (IOL). In either case, the corneal curvature correction and the IOL orientation need to be properly aligned relative to the astigmatic axis of the eye. To accomplish this, a conventional procedure is to first measure the astigmatic axis of the eye with a topographer, then mark the orientation of the astigmatic axis with ink marks or other marks on the cornea. Then, a correction action is performed either to the cornea or to the crystalline lens to correct the astigmatism. In the case of performing a correction action to the cornea, a strain relaxing incision is made to render the cornea curvature more spherical. In the case of performing a correction action to the crystalline lens, the crystalline lens is replaced by a toric IOL, inserted in a direction that counter-acts the astigmatism.

In either case, a problem may arise due to cyclotorsion of the eyes when the measurement of the astigmatic axis is done with the patient in an upright position (e.g. sitting), and the correction action (relaxation of the cornea or insertion of the toric IOL) is done when the patient is in a supine position (lying down). Cyclotorsion, which is a rotation of the eye about the visual axis, is common when a person lies down from an upright position. As described above, one solution for this problem is by marking the eye after the measurement using the topographer.

Another method to solve the problem, without marking the eye, is to create an angular association between two images of the same eye, the first taken when the patient is in an upright position, and the second of the same patient in a supine position, by comparing iris patterns in the two images. This association can then be used to map the measured astigmatic axis from the upright image to the image taken in the supine position. This is referred to as iris registration between two images of the eye to find the relative rotation of the eye in the two images. Conventional iris registration algorithms are typically computationally expensive.

SUMMARY OF THE INVENTION

The present invention is directed to an iris registration method that substantially obviates one or more of the problems due to limitations and disadvantages of the related art.

Embodiments of the present invention provide a method to perform iris registration between two images of the iris based on minimizing the Hamming distance in a sequence of relatively shifted rubber sheet representations of the original images. This method is both accurate and computationally cheap.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides an ophthalmic laser system for treating a patient's eye, which includes: a laser source configured to generate a pulsed laser beam; an optical delivery system coupled to the laser source, configured to receive and direct the pulsed laser beam; a camera coupled to the optical delivery system, configured to obtain images of the eye; and a processor coupled to the laser source, the optical delivery system, and the camera, configured to perform a process which includes: obtaining a measured astigmatism axis orientation of the eye, which has been measured while the patient is in an upright position; obtaining a first iris image of the eye, which has been captured while the patient is in the upright position; controlling the camera to capture a second iris image of the eye while the patient is in a supine position; computing a cyclotorsion rotation angle of the eye based on the first and second iris images, including: (a) for each of the first and second iris images: (a1) identifying an iris region of the iris image which corresponds to an iris of the eye between a pupil boundary and a limbus; (a2) transforming the iris region into a rectangular image, wherein a radial coordinate in the iris image is mapped to a vertical coordinate of the rectangular image, and an angular coordinate in the iris image is mapped to a horizontal coordinate of the rectangular image, and wherein the pupil boundary and the limbus are respectively mapped to two horizontal edges of the rectangular image; (a3) applying a horizontal one dimensional band-pass filter to each horizontal line of the rectangular image to generate a transformed rectangular image; and (a4) binarizing each horizontal line of the transformed rectangular image to generate a binary rectangular image, whereby a first binary rectangular image and a second binary rectangular image having same dimensions are generated from the first and second iris images, respectively; (b) comparing the first and second binary rectangular images at a series of relative horizontal shifts to determine an optimum horizontal shift value that produces a highest similarity between the first and second binary rectangular images; and (c) computing the cyclotorsion rotation angle of the eye between the first and second iris images based on the optimum horizontal shift value; and while the patient is in the supine position, controlling the laser source and the optical delivery system based on the measured astigmatism axis orientation and the computed cyclotorsion rotation angle to deliver the pulsed laser beam into the eye.

In another aspect, the present invention provides a method for treating a patient's eye, implemented in an ophthalmic laser system, the method including the above steps.

It is to be understood that both the foregoing general description and the following detailed description are exemplary and explanatory and are intended to provide further explanation of the invention as claimed.

BRIEF DESCRIPTION OF DRAWINGS

FIGS. 2A-8C are various images and plots related to the iris registration method according to embodiments of the present invention, in which:

FIGS. 2A and 2B show two iris images captured with a patient in the upright position and supine position, respectively.

FIG. 7 shows the Hamming distance between the two binary rubbersheet images of FIGS. 6A and 6B as a function of relative horizontal shift.

FIG. 8C shows a binarized profile of the profile in FIG. 8B.

DETAILED DESCRIPTION OF THE INVENTION

Figure 1:
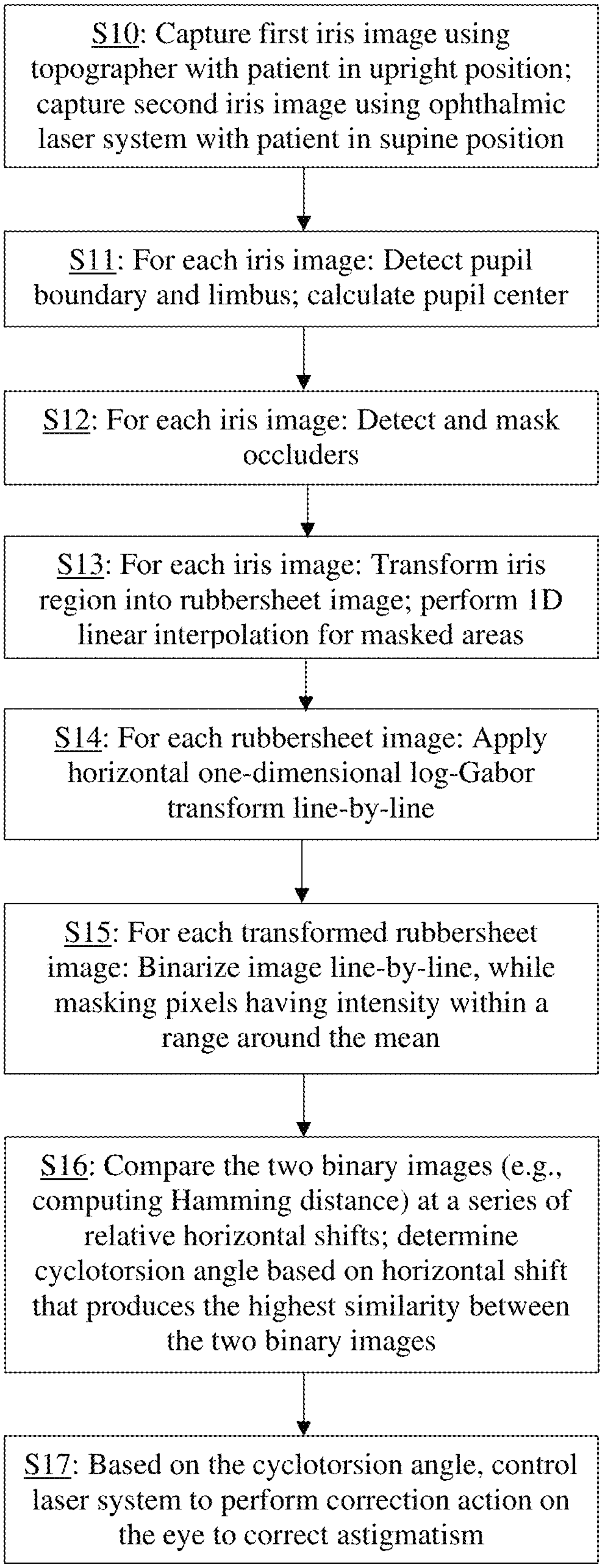
FIG. 1 schematically illustrates an iris registration method according to an embodiment of the present invention.

Embodiments of the present invention provide methods to perform iris registration between two eye images based on minimizing the Hamming distance in a sequence of relatively shifted rubber sheet representations of the original images. This method is both accurate and computationally inexpensive. The iris registration method is described with reference to the flow chart in FIG. 1.

First, two iris images are captured, the first using a topographer while the patient is in an upright position, the second using an imaging subsystem of an ophthalmic laser system while the patient is in a supine position (step S10). Topographers are generally known in the art and more detailed descriptions are omitted here. Ophthalmic laser systems are also generally known, and a more detailed description of an exemplary ophthalmic laser system is provided later. The imaging subsystem of the ophthalmic laser system may be, for example, a video camera or other cameras. A patient interface device may be used to couple the eye to the ophthalmic laser system when capturing the second image.

Figure 2A:
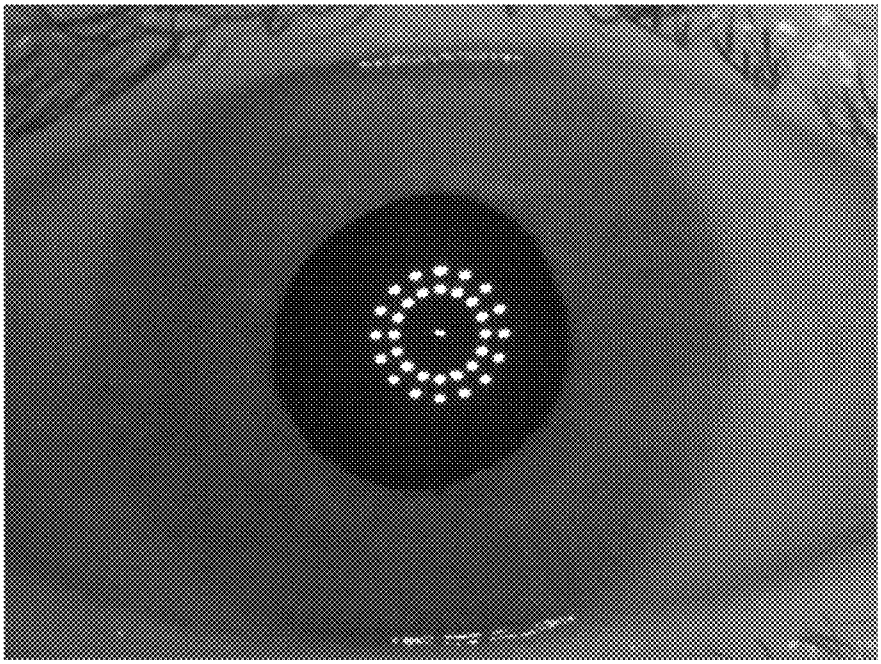
Figure 2B:
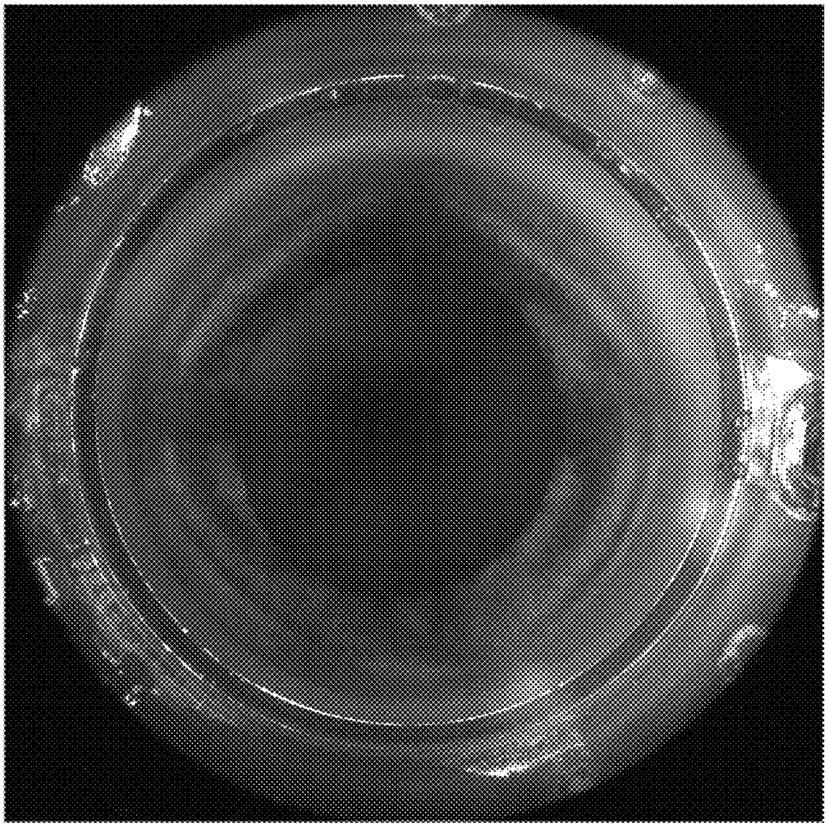

FIG. 2A shows an example of an eye image captured by the topographer (upright position); FIG. 2B shows an example of an eye image captured by the ophthalmic laser system (supine position). The two iris images are converted to grayscale images if they are not originally captured as grayscale images.

In practice, eye measurements using the topographer are performed first, and the first iris image captured by the topographer is imported into a control computer of the ophthalmic laser system. The control computer controls the laser system to capture the second iris image, performs the iris registration method, and then controls the laser system to perform desired treatment including astigmatism treatment. Thus, the subsequent steps described below are preferably performed by the control computer of the ophthalmic laser system. They may alternatively be performed by a stand-alone computer and the result is then transferred to the laser system to control the subsequent treatment.

It should be noted, however, that the iris registration method described here applies to two iris images captured by any relevant apparatus with the patient in any defined positions.

Figure 3A:
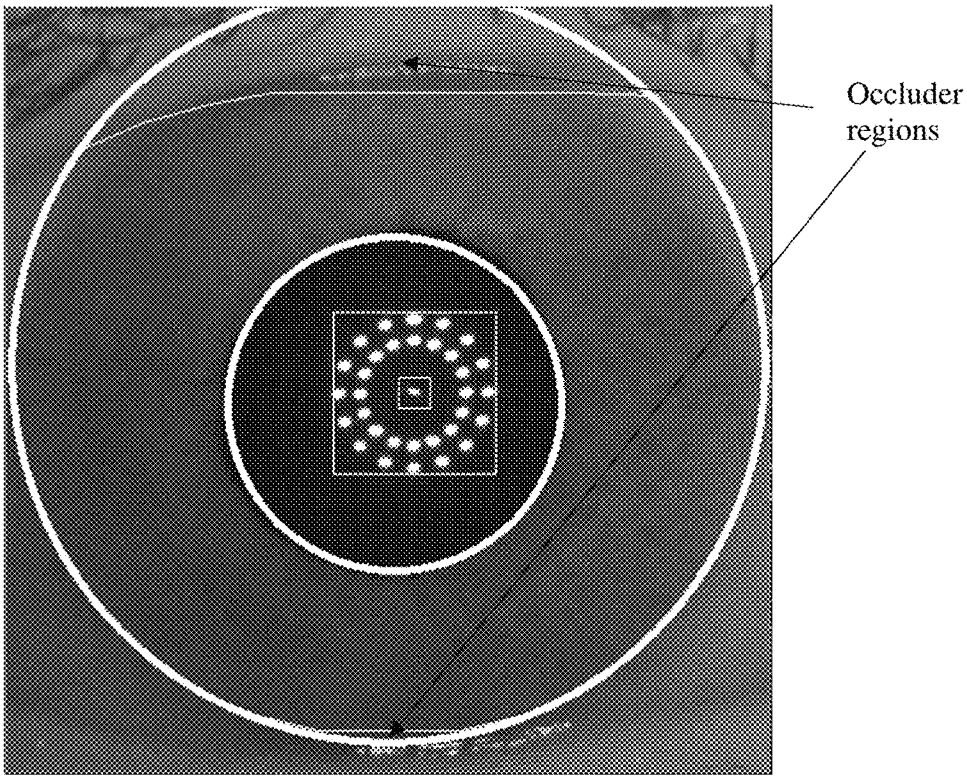
FIGS. 3A and 3B show the two iris images of FIGS. 2A and 2B, respectively, with various features indicated.
Figure 3B:
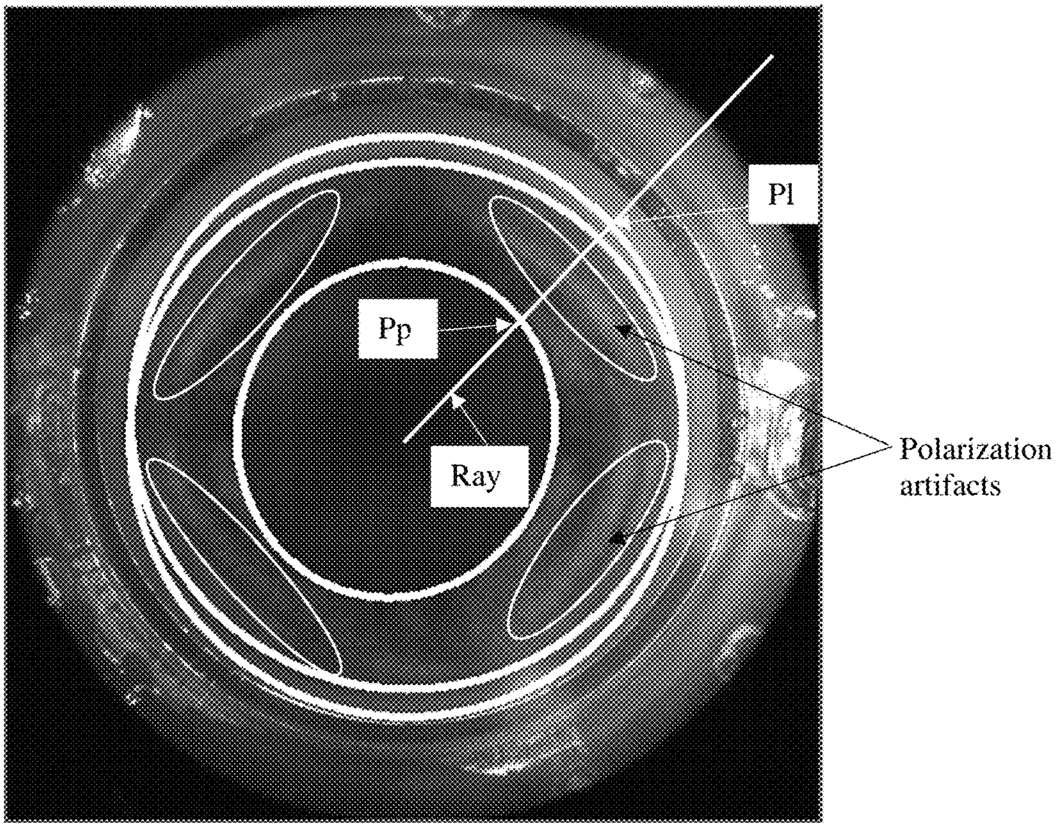

For each image, the pupil boundary and the limbus are detected, and the pupil center is calculated (step S11). Any suitable image processing methods may be used for pupil boundary and limbus detection. For example, an edge detection algorithm may be applied to identify edges in the image, and the detected edges are fitted to two circles or ellipses to identify the pupil boundary and the limbus. The pupil center is defined as the center of the circle or ellipse that is deemed the pupil. The iris region of the image is the ring shaped (circular or elliptical, concentric or non-concentric) region between the pupil boundary and the limbus. FIGS. 3A and 3B show the same iris images as FIGS. 2A and 2B, with the pupil boundary and limbus indicated.

Preferably, each iris image is also analyzed to identify various occluders that may be present in the image (step S12), such as eyelids blocking parts of the iris, which often occurs in the first (topographer) image (see FIG. 3A), or parts of a patient interface device used to couple the eye to the ophthalmic laser system when capturing the second image (see FIG. 3B). Image pixels in areas corresponding to the occluders are masked.

The occluder areas may be detected manually, or automatically by an image processing algorithm, or by a combined manual and automatic method. One algorithm for automatically detecting eyelids is described in more detail later.

Then, for each iris image, the iris region is transformed to a rectangular image, referred to as the rubbersheet (step S13). This step maps the iris region in the original image from its ring shape to a rectangular shape. This is done by means of the "rubbersheet" transform, which maps the radial coordinate in the original image to the vertical coordinate in the rectangular rubbersheet, and the angular coordinate in the original image to the horizontal coordinate in the rubbersheet. The pupil boundary and the limbus (their entire circumferences) are respectively mapped to the two horizontal edges of the rectangular rubbersheet. The two rubbersheets for the two iris images are defined to have the same dimensions.

In the simplest example, when the limbus and the pupil are circular and concentric, the iris perfectly maps to a rectangular sheet. When the limbus and/or the pupil are not circular and/or not concentric (as seen in the example in FIG. 3B), the rubbersheet is constructed from a plurality of rays that trace from the center of the pupil. Each ray intersects the pupil boundary and the limbus at points Pp and Pl, respectively (see FIG. 3B). The grayscale intensity profile of the image along the ray between Pp and Pl is mapped to the full vertical length of the rubbersheet, to form a single column in the rubbersheet image. The plurality of rays are evenly distributed in full 360 degrees around the pupil center. In preferred embodiments, the mapping of the radial coordinate to the vertical coordinate is a linear mapping. The grayscale intensity of each pixel of the rubbersheet is calculated by linear interpolation from grayscale intensities of pixels in the original image near the mapped position.

Figure 4A:
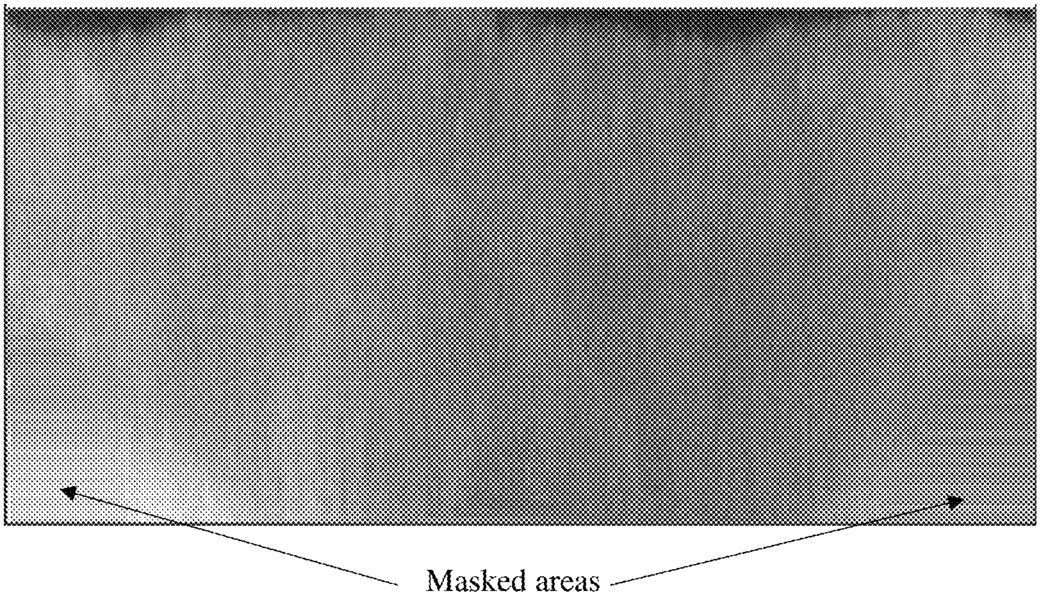
FIGS. 4A and 4B show two rubbersheet images corresponding to the two iris images of FIGS. 2A and 2B, respectively.
Figure 4B:
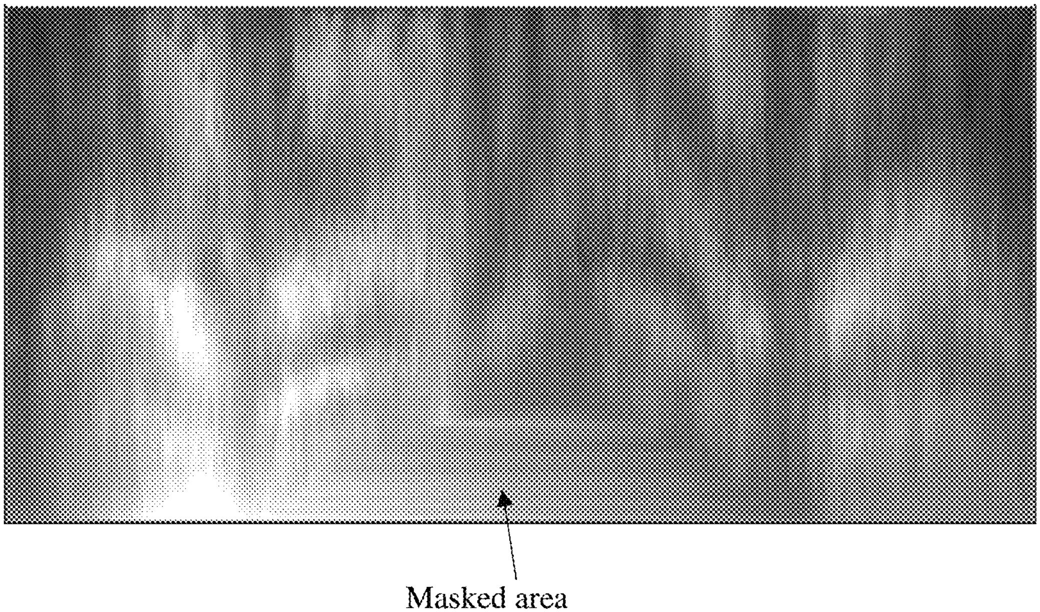

FIG. 4A shows a rubbersheet representation of the iris of the image captured by the topographer (FIG. 2A). FIG. 4B shows a rubbersheet representation of the iris of the image captured by the ophthalmic laser system (FIG. 2B). In these examples, the pupil boundary is mapped to the top edge and the limbus to the bottom edge of the rubbersheet. It is noted that the rubbersheet transform is insensitive to the amount of pupil dilation, as the two iris images are transformed to rubbersheets having the same dimensions.

The masked areas in the rubbersheet images corresponding to the masked areas in the iris images can be seen in FIGS. 4A and 4B. In some embodiments, the shape of the occluder in each rubbersheet image is saved in a binary image having the same size as the rubbersheet to keep track of the occluded (masked) pixels. To prepare for the next step, the pixel values in the masked areas in the rubbersheet images are replaced with interpolated values. More specifically, for each horizontal line segment of the rubbersheet image that lies in a masked area, a one-dimensional interpolation (e.g. a linear interpolation) is performed, using pixel values at the two ends of the line segments, to replace the pixel values. The effect of the linear interpolation and pixel value replacement in the masked areas may be seen in FIGS. 4A and 4B in the form of horizontal streaks.

Then, for each of the rubbersheet images, a horizontal one-dimensional log-Gabor transform is applied to the rubbersheet image in a line-by-line manner (step S14). In other words, for each individual horizontal line of the image, a one-dimensional log-Gabor transform G(f) is applied, independent of the transform applied to the other lines. The one-dimensional log-Gabor transform has the following frequency response:

$$G(f) = \exp\left(\frac{-(\log(f/f_0))^2}{2(\log(\sigma/f_0))^2}\right)$$

where f is the harmonic number, and $f_0$ (center frequency) and $\sigma$ (bandwidth) are parameters of the transform. The same parameter values are used for the transforms of all lines. The values of the parameters may be selected using empirical methods, for example, by comparing rotation angles calculated by the algorithm using trial parameter values against rotation angles determined manually. In some examples, the value of $f_0$ is between 17 and 512 and the value of $\sigma$ is between 0.05 and 30. In one particular implementation example, $f_0$ was 23.8 and $\sigma$ was 9.52. It should be noted that the invention is not limited to these examples, and any suitable parameters for the one-dimensional log-Gabor transform may be used.

Figure 5A:
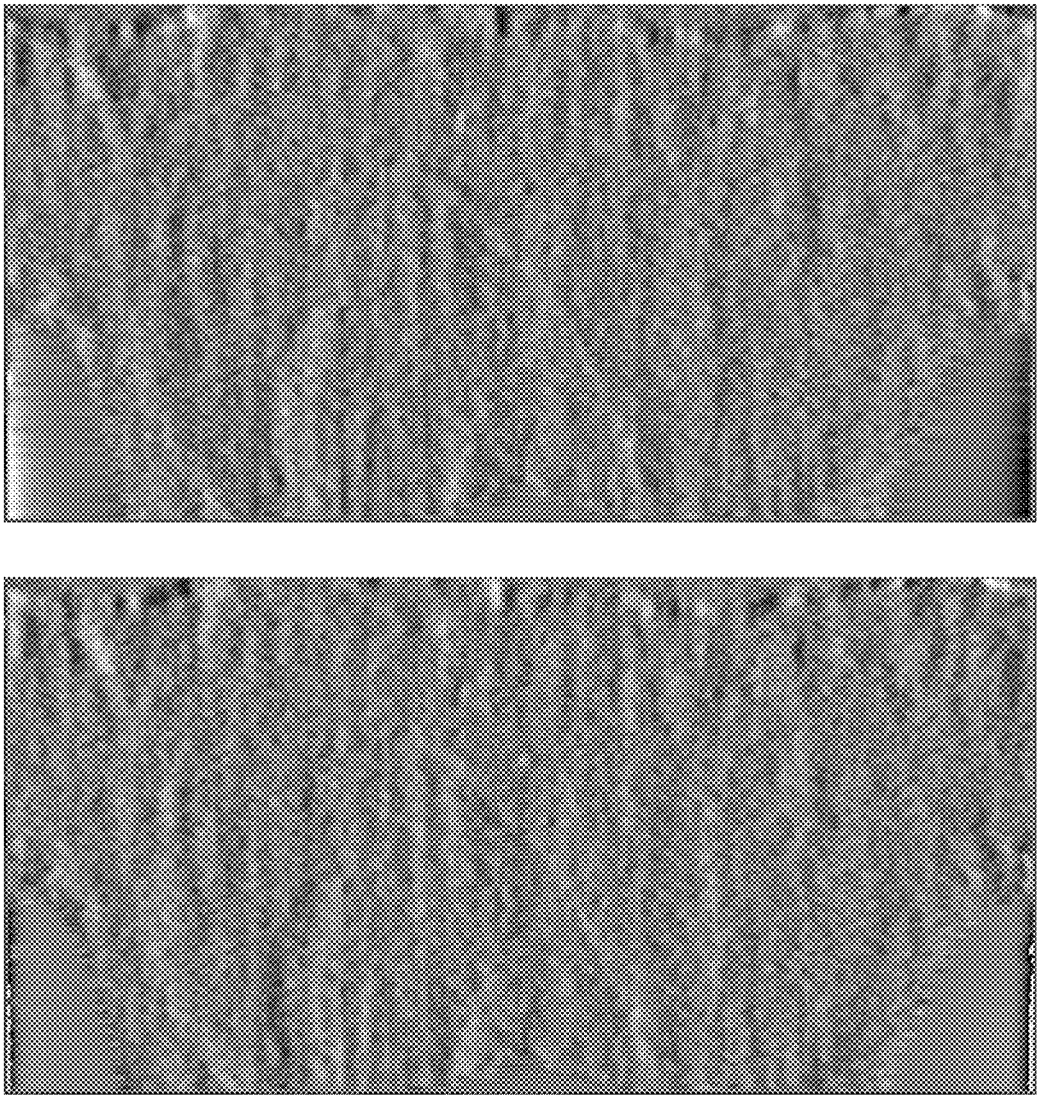
FIGS. 5A and 5B show two transformed rubbersheet images corresponding to the two rubbersheet images of FIGS. 4A and 4B, respectively, after one-dimensional log-Gabor transform.
Figure 5B:
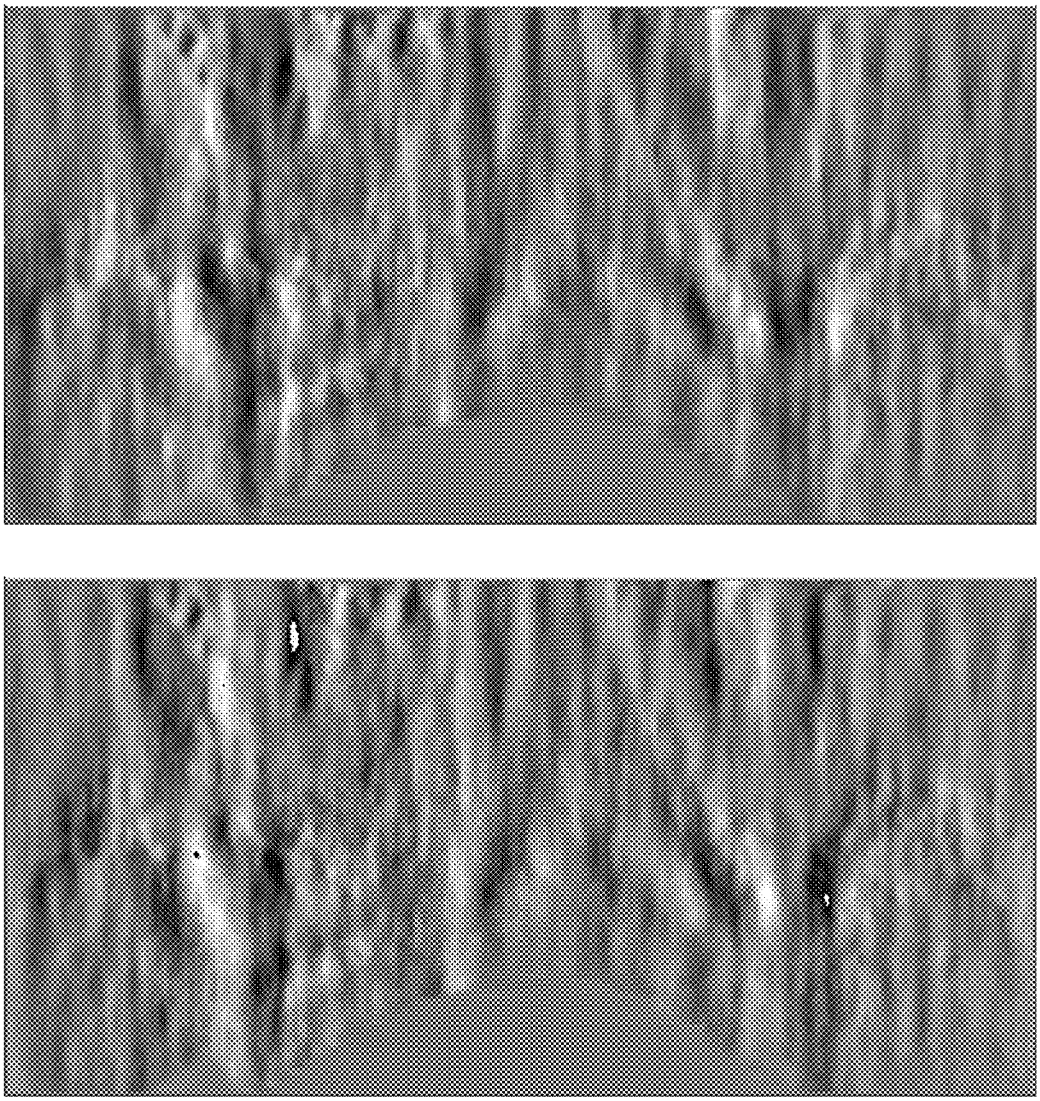

FIGS. 5A and 5B show transformed rubbersheet image after applying the one-dimensional log-Gabor transform to the rubbersheet images of FIGS. 4A and 4B, respectively. In each of FIGS. 5A and 5B, the top image is the real part of the transform and the bottom image is the imaginary part of the transform. Generally speaking, the one-dimensional log-Gabor transform servers as a band-pass filter that retains primarily only image information from the iris features in the rubbersheet image. Low-frequency information, such as the light polarization artifacts that tend to be present in the supine image, are suppressed.

For example, in FIGS. 2B and 3B (iris image captured by the ophthalmic laser system), four areas of polarization artifacts can be seen (indicated by the four ovals in FIG. 3B), in the form of diffused light-gray colored bands distributed in the angular direction; they correspond to the four diffused light-gray colored features in the rubbersheet image of FIG. 4B. As seen in FIG. 5B, these low-frequency artifacts are significantly reduced or removed by the log-Gabor filtering, while high-frequency features representing the characteristic iris pattern of the eye are preserved.

In alternative embodiments, other one-dimensional transforms that serve as band-pass filters may be applied, such as one-dimensional Gabor transform.

The log-Gabor-transformed rubbersheet images are grayscale images. Next, each of the transformed rubbersheet images is binarized to generate a binary rubbersheet (step S15). The binarization is performed line-by-line for individual horizontal lines. For each horizontal line, the mean grayscale pixel value of the line is calculated, and the pixels of that line are binarized using the mean value as a threshold. In other words, pixels with grayscale values at or above the threshold are assigned the one binary value (e.g. "1"), and pixels with grayscale values below the threshold are assigned the other binary value (e.g. "0"). In an alternative embodiment, two threshold values are used for the binarization, e.g., pixels with grayscale values at or above mean+δ1 are assigned one binary value and pixels with grayscale values below mean−δ2 are assigned the other binary value, where δ1 and δ2 are parameters. Pixels with grayscale values between the two thresholds are masked and will not be used in the subsequent processing steps. The values of δ1 and δ2 reflect the confidence level of pixel values being black or white. δ1 and δ2 may be equal or non-equal, and both may be zero (i.e., essentially no mask). Note that the occluded areas masked in step S14 continue to be masked and are not used in the binarization step.

Figure 6A:
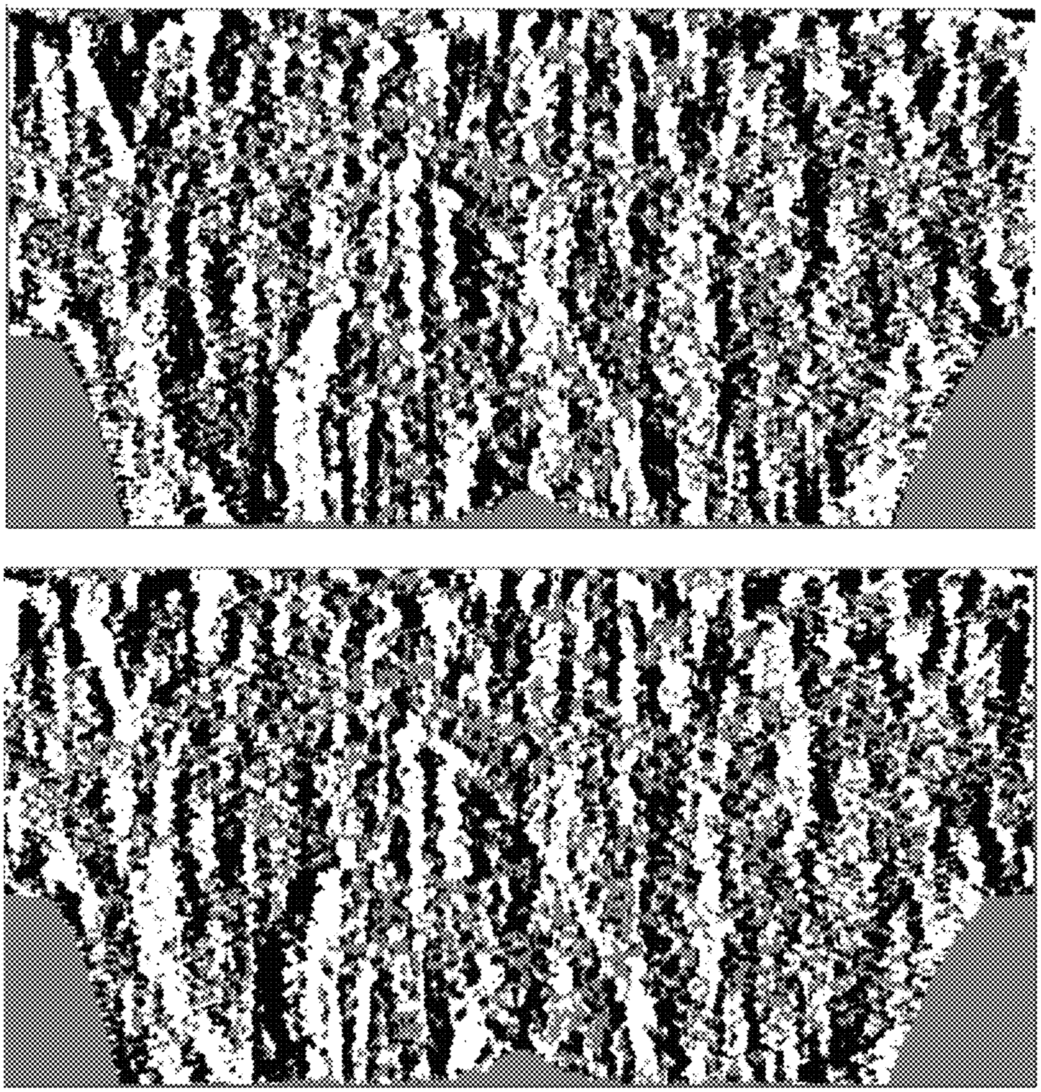
FIGS. 6A and 6B show two binary rubbersheet images corresponding to the two transformed rubbersheet images of FIGS. 5A and 5B, respectively, after binarization.
Figure 6B:
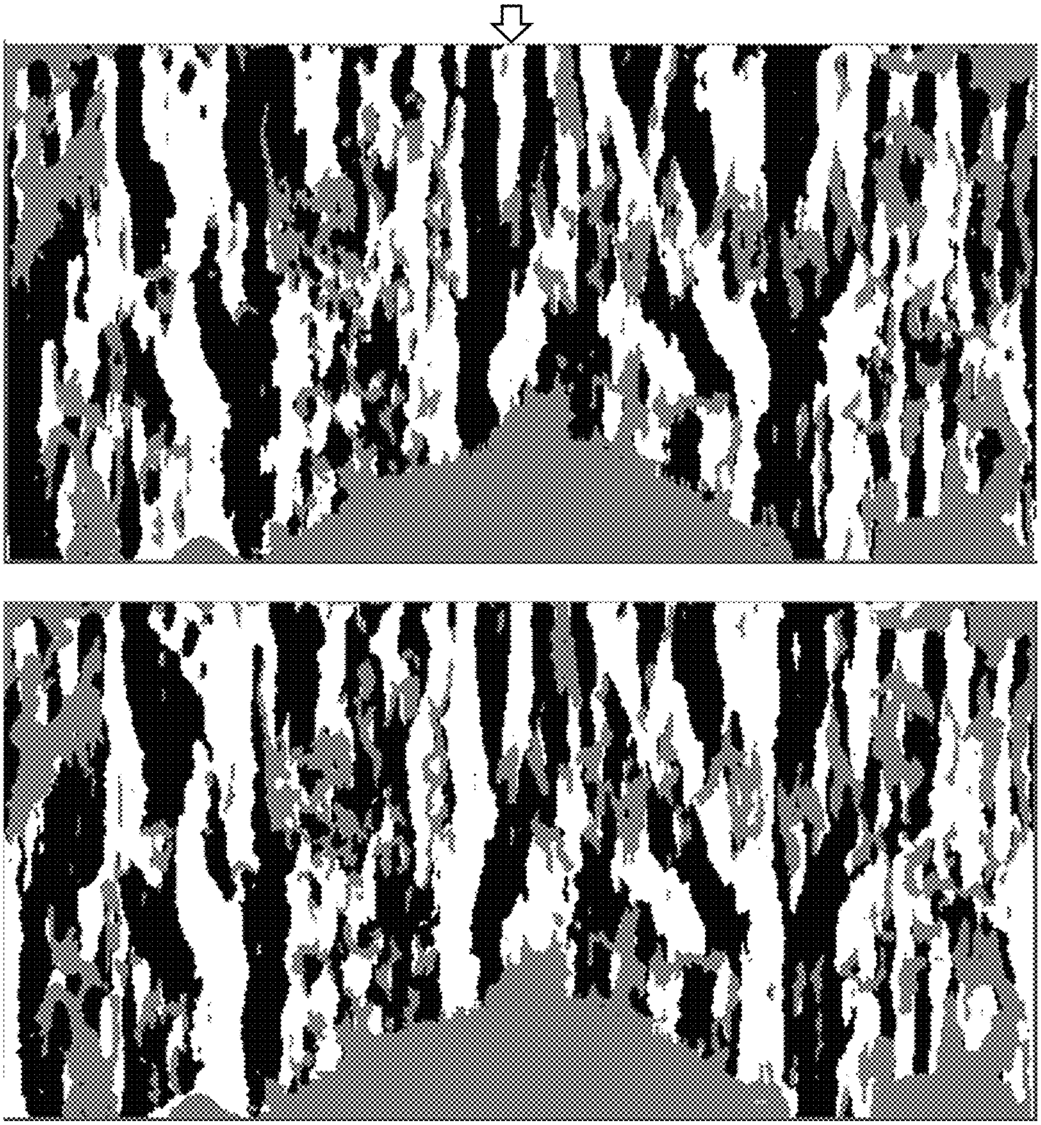

FIGS. 6A and 6B show binarized rubbersheet images corresponding to the transformed rubbersheet images of FIGS. 5A and 5B, respectively. Pixels assigned the two binary values are shown as white and black ones, and masked pixels are shown as gray ones. The values of the threshold parameters may be determined empirically. In this example, both threshold values were set to 0.3.

Then, the two binary images are compared at a series of relative horizontal shifts, to determine the horizontal shift value that produces the highest similarity between the two binary images (step S16). In a preferred embodiment, the comparison of the two binary images (which have the same size) is done by using the Hamming distance, which counts the number of pixels that have different values in two binary images. A horizontal shift shifts the columns of the image by a defined number of columns in either direction, with wrap-around. E.g., a shift of k column means that an original column at position j is shifted to column position j+k (mod N), where N is the total number of columns in the image.

More specifically, in step S16, the second binary image is shifted by k columns, and the Hamming distance between the first binary image and the shifted second binary image is calculated as H(k); the operation is repeated for k=+−1, +−2, . . . . In practice, the shift is performed within a k range that corresponds to a predefined angular range of the relative rotation of the original iris images, for example, from −30 degrees to 30 degrees. Then, the shift that produces the minimum Hamming distance value is identified.

Note that when calculating the Hamming distance, pixels that are masked during the binarization step in either of the two binary images are disregarded in the calculation. The Hamming distance is normalized by the total number of pixels actually used in the calculation.

Figure 7:
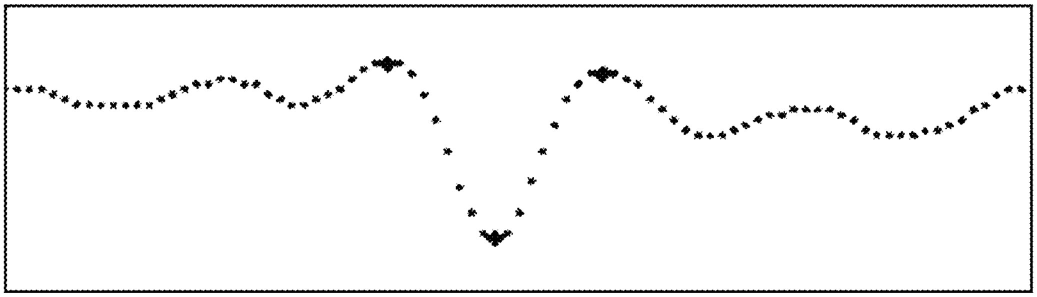

FIG. 7 shows the Hamming distance as a function of the shift, H(k), for two binary rubbersheet images such as those in FIGS. 6A and 6B. The horizontal shift value corresponding to the minimum Hamming distance is identified from the H(k) curve, and is deemed the relative rotation between the first and second original iris images, i.e., the cyclotorsion angle generated when the patient lied down.

In addition, a figure of merit may be computed from the Hamming distance curve as an indication of the confidence level in the determination of the minimum H position. This may be done by comparing the minimum H value with the rest of the Hamming distance curve. In one example, a trough area, defined as the area between the two local maximums on the two sides of the minimum, is excluded and a mean value is calculated for the remaining portion of the Hamming distance curve; then, the depth of the minimum H value measured from the mean of the remaining portion is compared to the depth of the minimum of the remaining portion of the Hamming distance curve, also measured from the mean of the remaining portion. The larger the ratio of the two depths, the higher the confidence level. In another example, the peak-to-valley height of the minimum H is compared to the average peak-to-valley height of other valleys of the curve; the larger the ratio of the two, the higher the confidence level.

Thereafter, the cyclotorsion angle obtained in step S16 may be used by the ophthalmic laser system to plan and execute the correction actions on the eye to correct astigmatism, such as making strain relaxing incisions on the cornea, replacing the crystalline lens by a toric IOL, etc. (step S17). These operations are performed by various components of the laser system under the control of the computer.

Figure 8A:
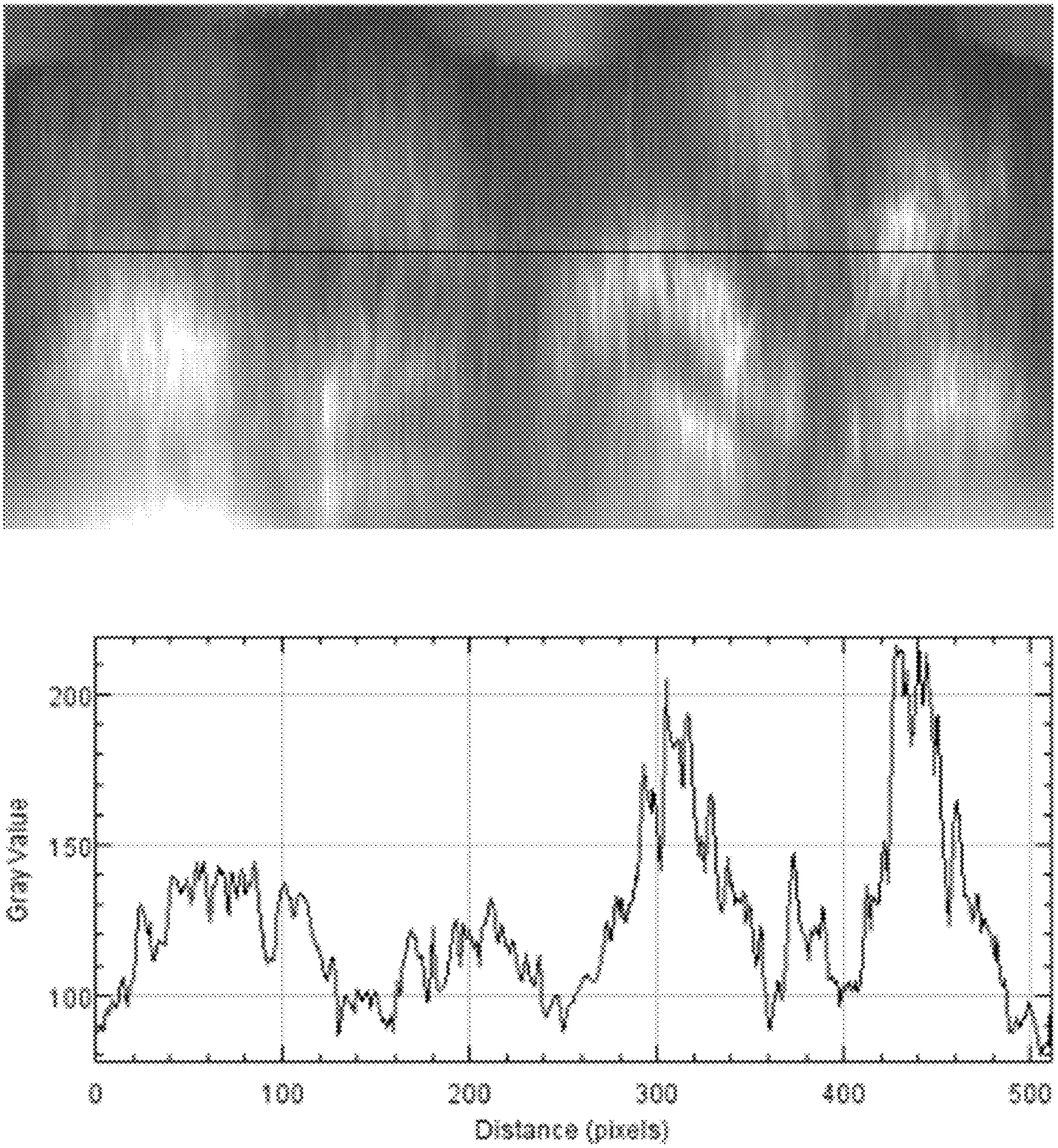
FIG. 8A shows a grayscale pixel value profile along one horizontal line in a rubbersheet image.
Figure 8B:
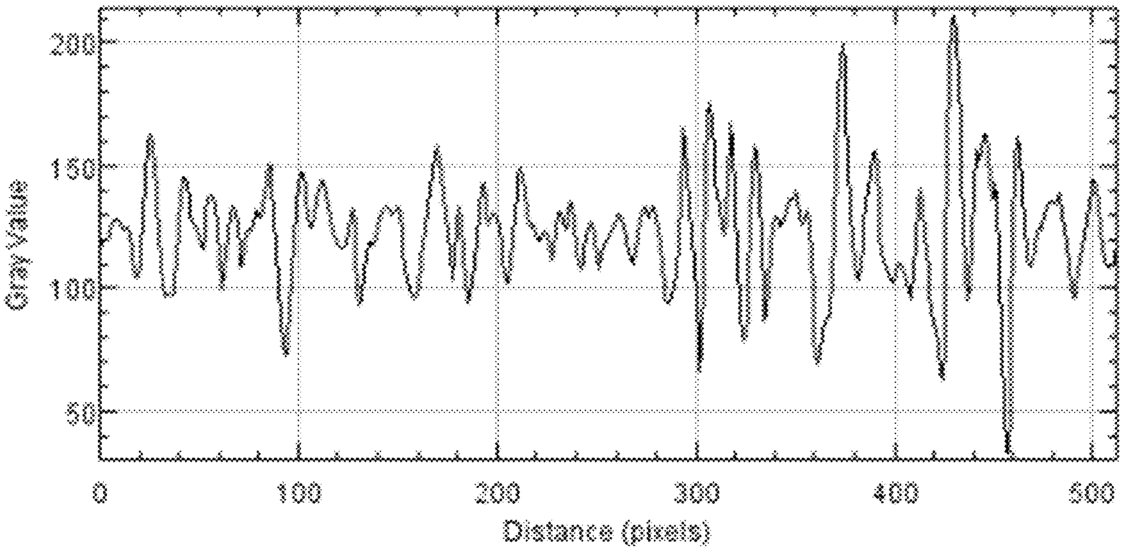
FIG. 8B shows a log-Gabor transformed grayscale value profile of the profile in FIG. 8A.
Figure 8C:
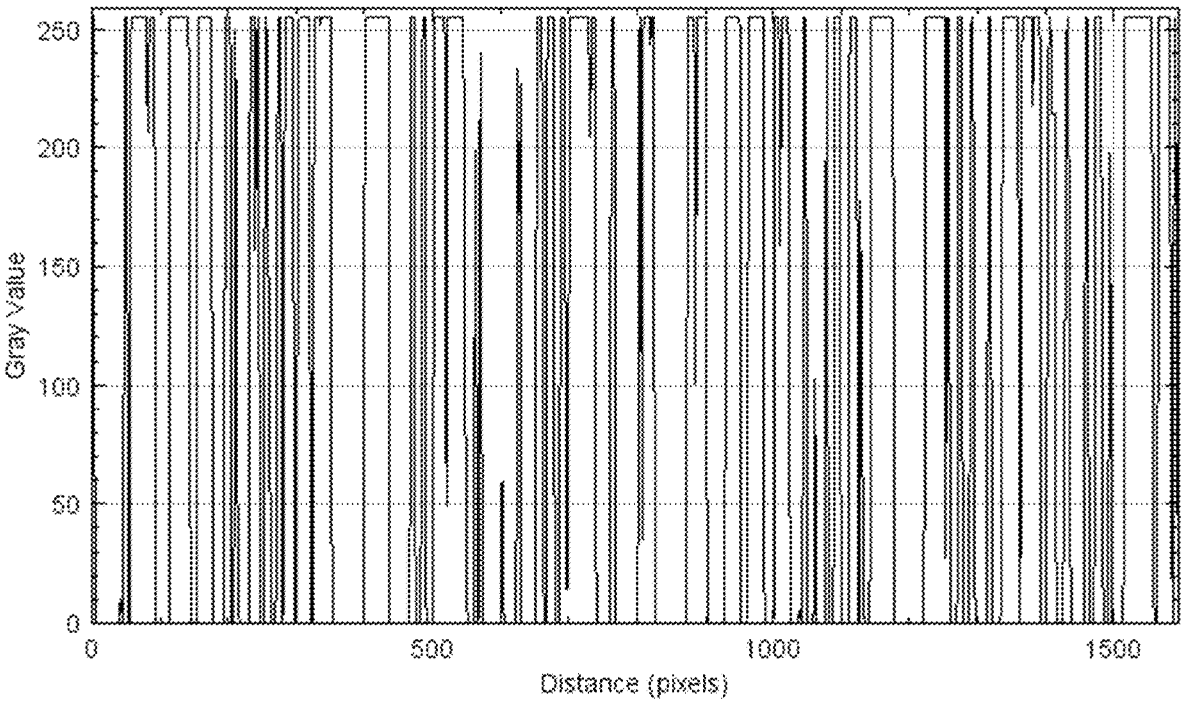

It should be emphasized that in step S14, a one-dimensional log-Gabor transform is applied, and the transform is applied to individual lines independent of each other. This is different from applying a two-dimensional Gabor or log-Gabor transform to the two-dimensional rubbersheet image, as is done in some known iris matching algorithms used in biometric identification. In biometric identification, iris features in both dimensions of the iris images should match to produce an iris match between two images, i.e., to determine that the two images are of the same iris of the same person. In the iris registration algorithm in embodiments of the present invention, on the other hand, the iris images are presumed to be of the same iris of the same patient, and the main objective is to rotationally align the two images to each other. The image features that manifest in the vertical direction of the rubbersheet (i.e., the radial direction of the iris) are not important for purposes of iris registration. Applying a series of one-dimensional log-Gabor filters to the rubbersheets line-by-line significantly simplifies the computation as compared to applying a two-dimensional log-Gabor filter to the two-dimensional image. Further, for similar reasons, the binarization step S16 is also performed line-by-line, so that the mean pixel value used to binarize each line is independent of the pixel intensities of the other lines. As an example, FIG. 8A shows a rubbersheet image and a grayscale pixel value profile along one horizontal line indicated in the rubbersheet image, FIG. 8B shows a log-Gabor transformed grayscale value profile of the profile in FIG. 8A, and FIG. 8C shows a binarized profile of the profile in FIG. 8B.

It is also noted that image comparison using binary operations has the advantage of being very fast, as compared to other methods such as image correlation, or least square image registration, such as the Lucas-Kanade algorithms.

Figure 9:
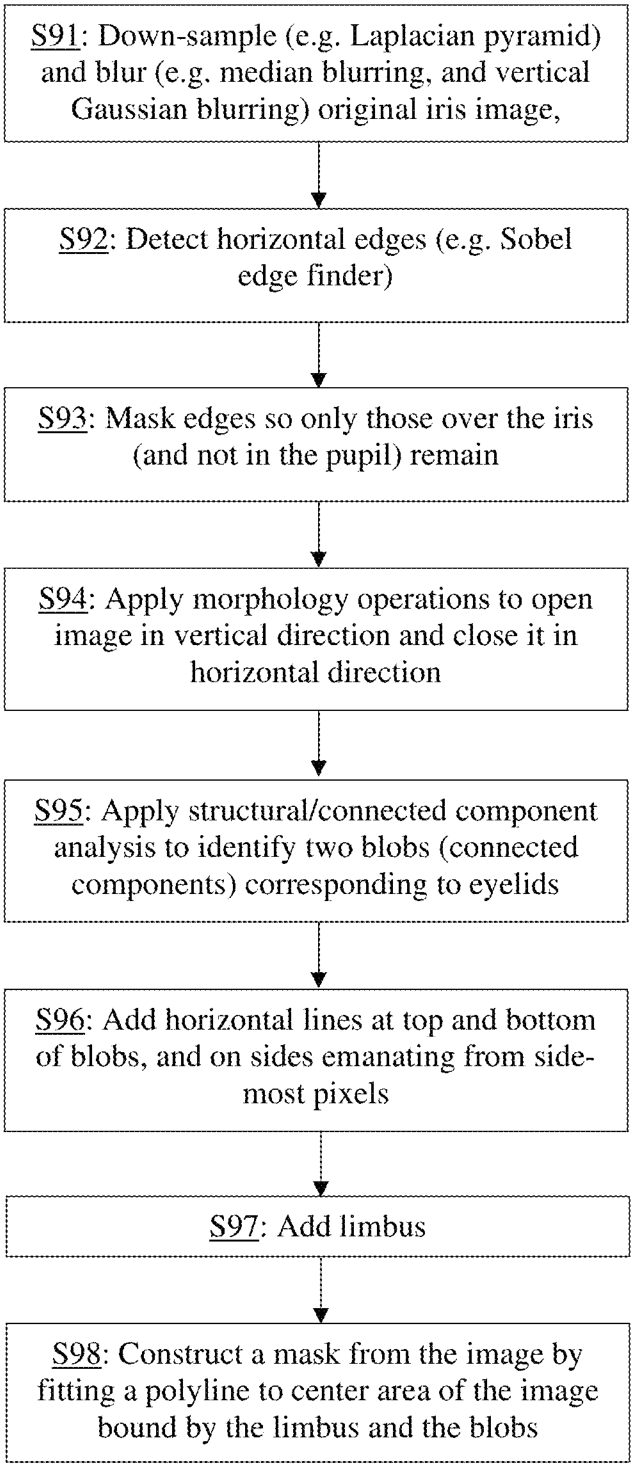
FIG. 9 schematically illustrates an eyelid detection method according to another embodiment of the present invention.

A method of detecting eyelids in an iris image is described now with reference to the flow chart in FIG. 9 and images in FIGS. 10A-H. This method may be used to implement S12 of the method of FIG. 1.

Figure 10A:
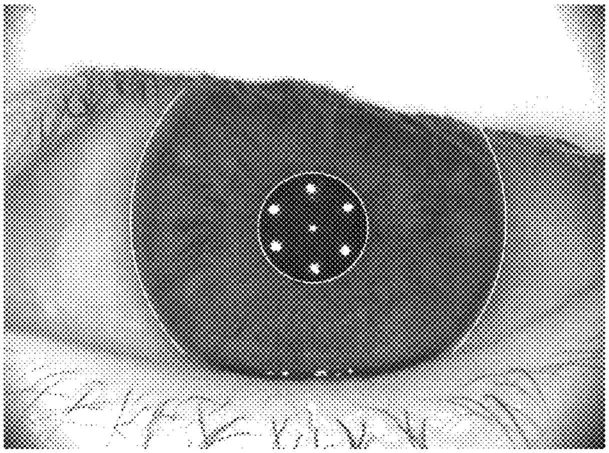
FIGS. 10A-10H show various images related to the eyelid detection method of FIG. 9.
Figure 10B:
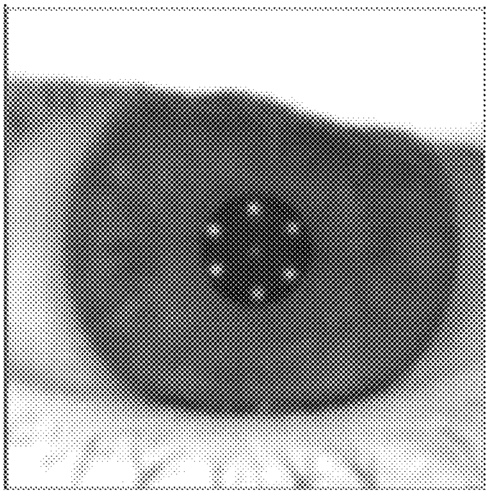
Figure 10C:
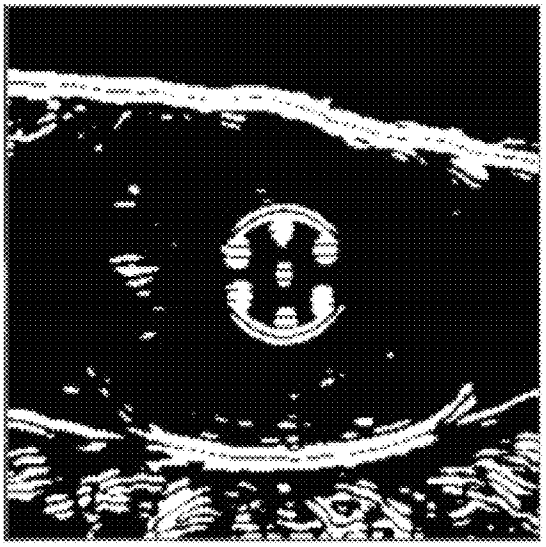

FIG. 10A shows an original eye image, where the eyelids obscure parts of the iris. The original image is first down-sampled and blurred (step S91). In a preferred embodiment, the original image down-sampled, for example, with a Laplacian pyramid. It is median blurred to smooth out the iris features, and then Gaussian blurred in the vertical direction only. FIG. 10B shows the image of FIG. 10A after the down-sampling and blurring step. Then, an edge detection method is applied to detect horizontal edges (step S92). In the preferred embodiment, a Sobel edge finder is applied to detect the second derivatives in the vertical direction only. The edge detection results (edge map) is a binary image, as shown in FIG. 10C. Then, a mask is applied so that edges outside of the limbus (e.g. the eye lashes near the bottom and the parts of the eyelid extending outside of the limbus) and edges inside the pupil are masked, so only edges over the iris are exposed by the mask (step S93). This step requires knowledge of the pupil boundary and limbus, which is previously detected (see step S12). The pupil boundary and limbus are indicated in the image of FIG. 10A.

Figure 10D:
Figure 10E:
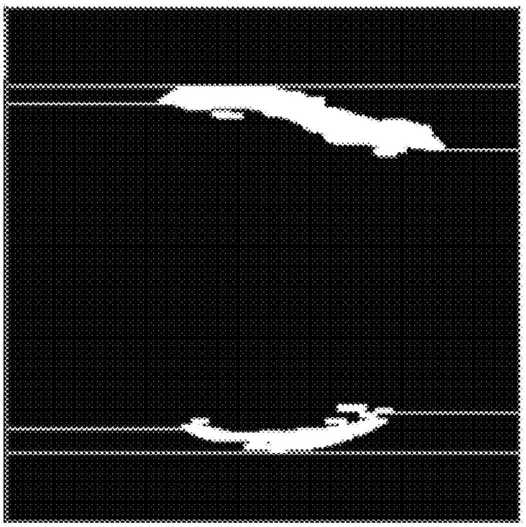
Figure 10F:
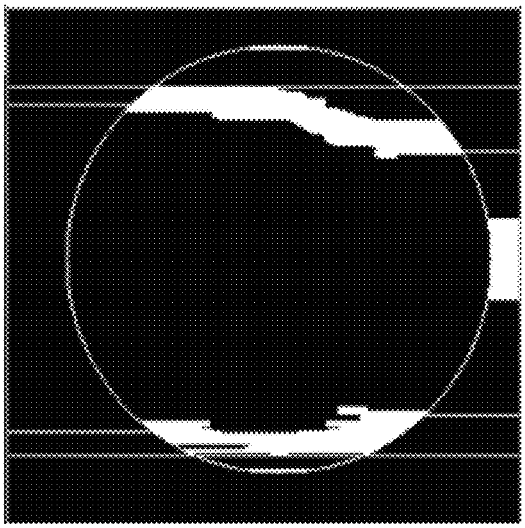
Figure 10G:
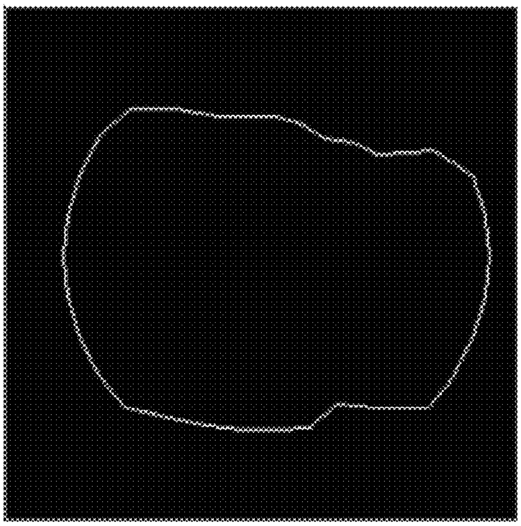
Figure 10H:
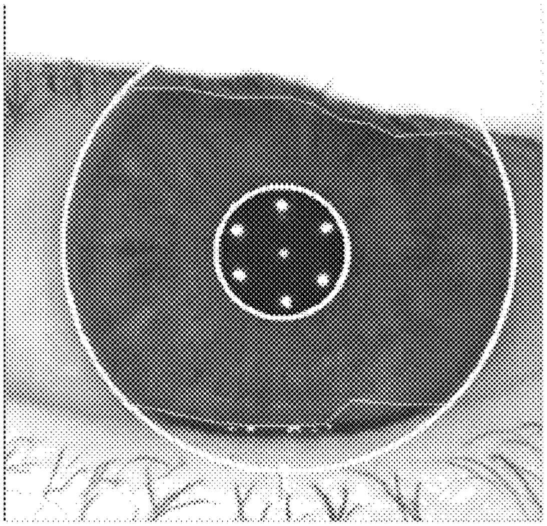

Morphology operations OPEN and CLOSE are then applied to the edge map to "open" it in the vertical direction and "close" it in the horizontal direction (step S94). FIG. 10D shows the image of FIG. 10C after the masking and the morphology operations. Structural/connected component analysis is applied to the image, where individual connected components are isolated, and analyzed depending on size and orientation, to identify the two blobs (connected components) corresponding to the eyelids (step S95). Horizontal lines are added at the top and bottom of the blobs, and on the sides emanating from the side-most pixels of each blob (step S96). The result is shown in FIG. 10E. These horizontal lines serve to create limits when creating the mask, especially in certain situations such as when only one eyelid blob is detected. The limbus is added to limit the detection (step S97). The result is shown in FIG. 10F. Note that additional morphological CLOSE operations were applied to the image of FIG. 10E prior to adding the limbus (optional step). Then, a mask is constructed from the image, by fitting a polyline to the center area of the image bound by the limbus and the blobs (step S98). FIG. 10G shows the mask thus constructed, and FIG. 10H shows the mask overlaid on the original image. This concludes the eyelid detection step.

As mentioned earlier, various steps of the iris registration method may be performed by a control computer of the ophthalmic laser system. When the laser system is separate from the topographer, the control computer obtains the first iris image, which has been captured by the topographer, as an input. A laser system 10 that may be used to practice embodiments of the present invention is now described in more detail with reference to FIGS. 11 and 12.

Figure 11:
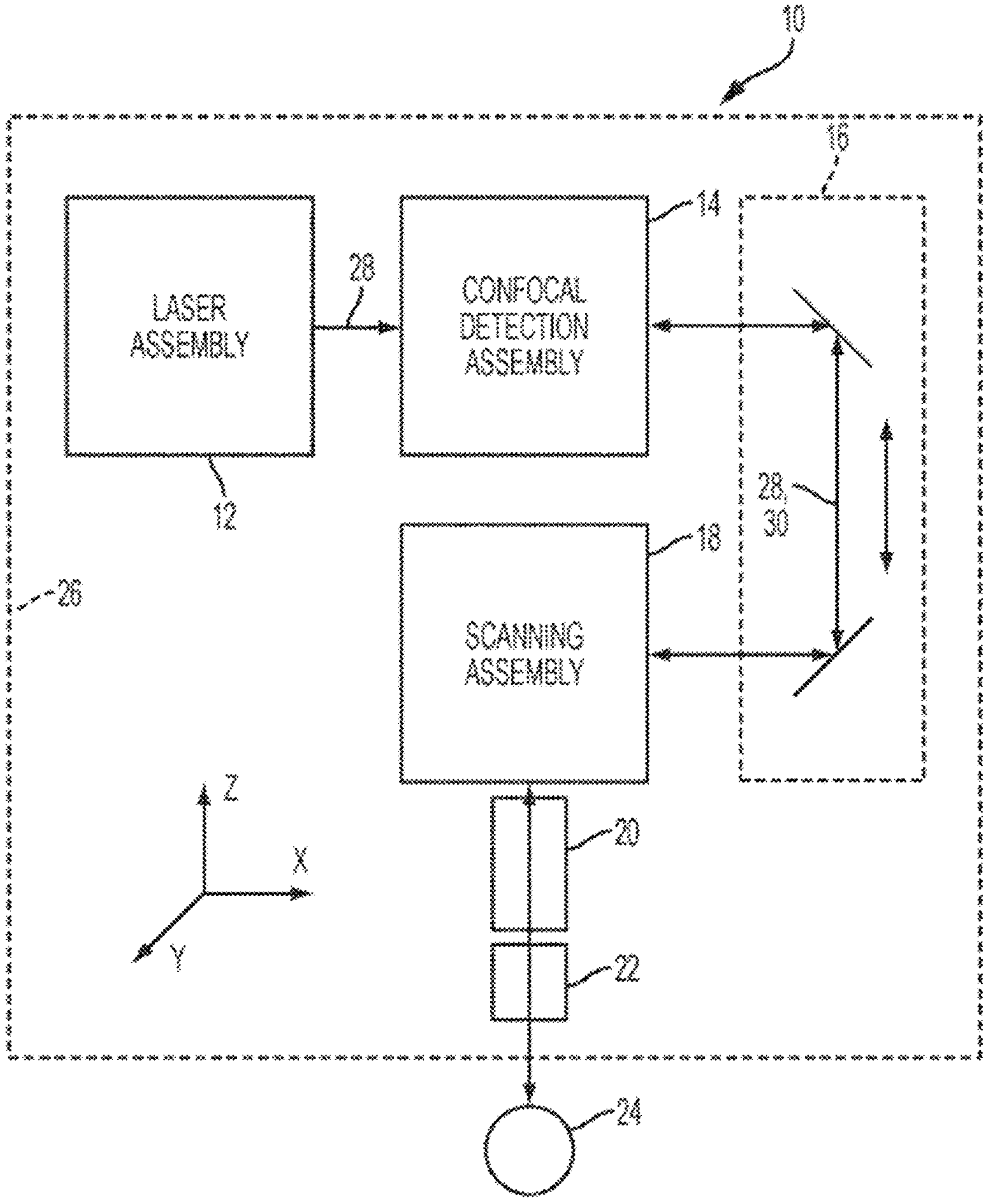
FIGS. 11 and 12 schematically illustrate an ophthalmic laser system that may be used to implement various methods according to embodiments of the present invention.

As shown in FIG. 11, the laser surgery system 10 may include a laser source/assembly 12, a confocal detection assembly 14, a free-floating mechanism 16, a scanning assembly 18, an objective lens assembly 20, and a patient interface device 22. The patient interface device 22 may be configured to interface with a patient's eye 24. The patient interface device 22 may be supported by the objective lens assembly 20, which may be supported by the scanning assembly 18, which may be supported by the free-floating mechanism 16. The free-floating mechanism 16 may have a portion having a fixed position and orientation relative to the laser assembly 12 and the confocal detection assembly 14. The laser beam 28 may propagate through the free-floating mechanism 16 along a variable optical path 30, which may deliver the beam 28 to the scanning assembly 18. An optical delivery system for receiving and directing the treatment beam may comprise some or all of the components coupled to the to the sub-nanosecond laser assembly 12. In some embodiments, the patient interface device 22 can be configured to be coupled to an eye of the eye 24 using vacuum. The laser surgery system 10 can further optionally include a base assembly 26 that can be fixed in place or be repositionable.

The electromagnetic radiation beam 28 emitted by the laser assembly 12 can include a series of laser pulses of any suitable energy level, duration, and repetition rate. In many embodiments, the laser assembly 12 incorporates sub-nanosecond laser technology where a short duration (e.g., approximately 10 ns to 1 picosecond in duration) laser pulse (with energy level in the tens of micro joules range) can be delivered to a tightly focused point to disrupt tissue, thereby substantially lowering the energy level required to image and/or modify an intraocular target as compared to laser pulses having longer durations. The laser assembly 12 may produce laser pulses having a wavelength suitable to treat and/or image tissue.

The laser assembly 12 may include control and conditioning components. In an embodiment, the control components may include a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. The conditioning components may include an adjustable zoom assembly and a fixed optical relay to transfer the laser pulses over a distance while accommodating laser pulse beam positional and/or directional variability, thereby providing increased tolerance for component variation.

In some embodiments, the scanning assembly 18 can include a Z-scan device and an XY-scan device. The laser surgery system 10 may be configured to focus the electromagnetic radiation beam 28 to a focal point that is scanned in three dimensions. The Z-scan device may be operable to vary the location of the focal point in the direction of propagation of the beam 28. The XY-scan device may be operable to scan the location of the focal point in two dimensions transverse to the direction of propagation of the beam 28. Accordingly, the combination of the Z-scan device and the XY-scan device can be operated to controllably scan the focal point of the beam in three dimensions, including: within a tissue, e.g., eye tissue, of the eye 24. The scanning assembly 18 may be supported by the free-floating mechanism 16, which may accommodate patient movement, induced movement of the scanning assembly 18 relative to the laser assembly 12 and the confocal detection assembly 14 in three dimensions.

Figure 12:
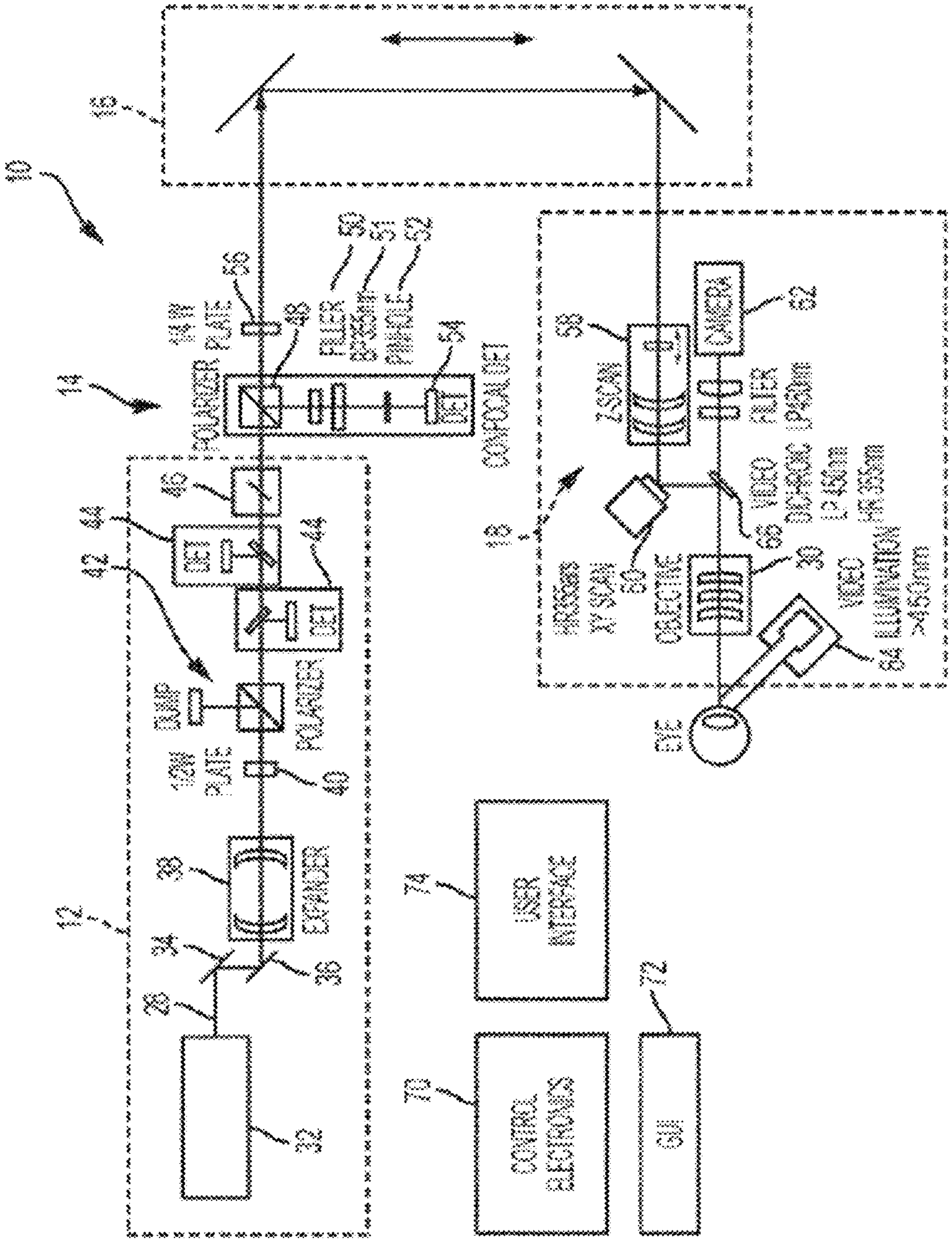

FIG. 12 schematically illustrates details of an embodiment of the laser surgery system 10. Specifically, example configurations are schematically illustrated for the laser assembly 12, the confocal detection assembly 14, and the scanning assembly 18. As shown in the illustrated embodiment, the laser assembly 12 may include an IR laser 32, alignment mirrors 34, 36, a beam expander 38, a one-half wave plate 40, a polarizer and beam dump device 42, output pickoffs and monitors 44, and a system-controlled shutter 46. The electromagnetic radiation beam 28 output by the laser 32 may be deflected by the alignment mirrors 34, 36. In many embodiments, the alignment mirrors 34, 36 may be adjustable in position and/or orientation so as to provide the ability to align the beam 28 with the downstream optical path through the downstream optical components. Next, the beam 28 may pass through the beam expander 38, which can increase the diameter of the beam 28. The expanded beam 28 may then pass through the one-half wave plate 40 before passing through the polarizer 42. The beam exiting the polarizer 42 may be linearly polarized. The one-half wave plate 40 can rotate this polarization. The amount of light passing through the polarizer 42 depends on the angle of the rotation of the linear polarization. Therefore, the one-half wave plate 40 with the polarizer 42 may act as an attenuator of the beam 28. The light rejected from this attenuation may be directed into the beam dump. Next, the attenuated beam 28 may pass through the output pickoffs and monitors 44 and then through the system-controlled shutter 46. By locating the system-controlled shutter 46 downstream of the output pickoffs and monitors 44, the power of the beam 28 can be checked before opening the system-controlled shutter 46.

The system 10 can be set to locate the anterior and posterior surfaces of the lens capsule and cornea and ensure that the laser pulse beam 28 will be focused on the lens capsule and cornea at all points of the desired opening. In the embodiment of FIGS. 11 and 12, a confocal detection assembly 14 is described, although other modalities are within the scope of the present invention. Imaging systems and techniques described herein, such as for example, Optical Coherence Tomography (OCT), Purkinje imaging, Scheimpflug imaging, structured light illumination, confocal backreflectance imaging, fluorescence imaging, ultrasound, or other ophthalmic or medical imaging modalities and/or combinations thereof, may be used to measure structures of the anatomical components of the eye, such as to determine the location and measure the thickness of the lens and lens capsule to provide greater precision to the laser focusing methods. The imaging modalities can perform 2D and 3D patterning. For example, an OCT scan of the eye can provide information about the shape of the cornea, the axial location of the anterior and posterior lens capsule, the boundaries of the cataract nucleus, as well as the depth of the anterior chamber. This information is then loaded into the control electronics 70, and used to program and control the subsequent laser-assisted surgical procedure. The information may also be used to determine a wide variety of parameters related to the procedure such as, for example, the upper and lower axial limits of the focal planes used for modifying the lens capsule, cornea, and synthetic intraocular lens implant, among others.

As shown in the illustrated embodiment, the scanning assembly 18 may include a Z-scan device 58 and an XY-scan device 60. The Z-scan device 58 may be operable to vary a convergence/divergence angle of the beam 28 and thereby change a location of the focal point in the direction of propagation of the beam 28. For example, the Z-scan device 58 may include one or more lenses that are controllably movable in the direction of propagation of the beam 28 to vary a convergence/divergence angle of the beam 28. The XY-scan device 60 may be operable to deflect the beam 28 in two dimensions transverse to the direction of propagation of the beam 28. For example, the XY-scan device 60 can include one or more mirrors that are controllably deflectable to scan the beam 28 in two dimensions transverse to the direction of propagation of the beam 28. Accordingly, the combination of the z-scan device 58 and the xy-scan device 60 can be operated to controllably scan the focal point in three dimensions, for example, within the eye of the patient.

As shown further in the illustrated embodiment, a camera 62 and associated video illumination 64 can be integrated with the scanning assembly 18. The camera 62 and the beam 28 may share a common optical path through the objective lens assembly 20 to the eye. A video dichroic 66 may be used to combine/separate the beam 28 with/from the illumination wavelengths used by the camera. For example, the beam 28 can have a wavelength of about 355 nm and the video illumination 64 can be configured to emit illumination having wavelengths greater than 450 nm. Accordingly, the video dichroic 66 can be configured to reflect the 355 nm wavelength while transmitting wavelengths greater than 450 nm.

The control electronics 70 controls the operation of and can receive input from the laser assembly 12, the confocal detection assembly 14, free-floating mechanism 16, the scanning assembly 18, the objective lens assembly 20, the patient interface 22, control panel/graphical user interface (GUI) 72, and user interface devices 74 via communication paths. The communication paths can be implemented in any suitable configuration, including any suitable shared or dedicated communication paths between the control electronics 70 and the respective system components.

The control electronics 70 can include any suitable components, such as one or more processors, one or more field-programmable gate array (FPGA), and one or more memory storage devices. The control electronics 70 is operatively coupled via the communication paths with the laser assembly 12, the confocal detection assembly 14, the free-floating mechanism 16, the scanning assembly 18, the control panel/GUI 72, and the user interface devices 74. In many embodiments, the control electronics 70 controls the control panel/GUI 72 to provide for pre-procedure planning according to user specified treatment parameters as well as to provide user control over the laser eye surgery procedure. The control electronics 70 can include a processor/controller that is used to perform calculations related to system operation and provide control signals to the various system elements. A computer readable medium can be coupled to the processor in order to store data used by the processor and other system elements. The processor interacts with the other components of the system as described more fully throughout the present specification. In an embodiment, the memory can include a look up table that can be utilized to control one or more components of the laser system surgery system.

The processor can be a general purpose microprocessor configured to execute instructions and data. It can also be an Application Specific Integrated Circuit (ASIC) that embodies at least part of the instructions for performing the method according to the embodiments of the present disclosure in software, firmware and/or hardware. As an example, such processors include dedicated circuitry, ASICs, combinatorial logic, other programmable processors, combinations thereof, and the like. The memory can be local or distributed as appropriate to the particular application. Memory can include a number of memories including a main random access memory (RAM) for storage of instructions and data during program execution and a read only memory (ROM) in which fixed instructions are stored. Thus, the memory provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

It will be apparent to those skilled in the art that various modification and variations can be made in the iris registration method and related apparatus of the present invention without departing from the spirit or scope of the invention. Thus, it is intended that the present invention cover modifications and variations that come within the scope of the appended claims and their equivalents.

The invention claimed is:

1. An ophthalmic laser system for treating a patient's eye, comprising:

a laser source configured to generate a pulsed laser beam;

an optical delivery system coupled to the laser source, configured to receive and direct the pulsed laser beam;

a camera coupled to the optical delivery system, configured to obtain images of the eye; and a processor coupled to the laser source, the optical delivery system, and the camera, configured to perform a process which includes:

obtaining a measured astigmatism axis orientation of the eye, which has been measured while the patient is in an upright position;

obtaining a first iris image of the eye, which has been captured while the patient is in the upright position;

controlling the camera to capture a second iris image of the eye while the patient is in a supine position;

computing a cyclotorsion rotation angle of the eye based on the first and second iris images, including:

(a) for each of the first and second iris images:

(a1) identifying an iris region of the iris image which corresponds to an iris of the eye between a pupil boundary and a limbus;

(a2) transforming the iris region into a rectangular image, wherein a radial coordinate in the iris image is mapped to a vertical coordinate of the rectangular image, and an angular coordinate in the iris image is mapped to a horizontal coordinate of the rectangular image, and wherein the pupil boundary and the limbus are respectively mapped to two horizontal edges of the rectangular image;

(a3) applying a horizontal one-dimensional band-pass filter to each horizontal line of the rectangular image to generate a transformed rectangular image; and (a4) binarizing each horizontal line of the transformed rectangular image to generate a binary rectangular image, whereby a first binary rectangular image and a second binary rectangular image having same dimensions are generated from the first and second iris images, respectively;

(b) comparing the first and second binary rectangular images at a series of relative horizontal shifts to determine an optimum horizontal shift value that produces a highest similarity between the first and second binary rectangular images; and (c) computing the cyclotorsion rotation angle of the eye between the first and second iris images based on the optimum horizontal shift value; and while the patient is in the supine position, controlling the laser source and the optical delivery system based on the measured astigmatism axis orientation and the computed cyclotorsion rotation angle to deliver the pulsed laser beam into the eye.

2. The ophthalmic laser system of claim 1, wherein for each of the first and second iris images, step (a2) includes tracing a plurality of rays from a pupil center, each ray intersecting the pupil boundary and the limbus at a first and a second point, respectively, and mapping a grayscale intensity profile of the iris image along each ray between the first and second points to a full vertical length of the rectangular image to form a column of the rectangular image.

3. The ophthalmic laser system of claim 2, wherein the mapping of the grayscale intensity profile from each of the plurality of rays to the full vertical length of the rectangular image is a linear mapping.

4. The ophthalmic laser system of claim 1, wherein the one-dimensional band-pass filter is a one-dimensional log-Gabor transform.

5. The ophthalmic laser system of claim 1, wherein for each of the first and second iris images, step (a4) includes, for each horizontal line of the transformed rectangular image:

calculating a mean of grayscale pixel values of the horizontal line; and binarizing each pixel of the horizontal line using the mean as a threshold.

6. The ophthalmic laser system of claim 1, wherein step (a4) includes, for each horizontal line of the transformed rectangular image:

calculating a mean of grayscale pixel values of the horizontal line; and binarizing each pixel of the horizontal line using two threshold values calculated from the mean, wherein pixels having grayscale pixel values between the two threshold values are masked; and wherein in step (b), pixels that are masked during the binarization step in either of the first or second binary rectangular images are disregarded in the comparison.

7. The ophthalmic laser system of claim 1, wherein step (b) includes, at each relative horizontal shift, computing a Hamming distance between first and second binary rectangular images as a measure of similarity.

8. The ophthalmic laser system of claim 1, wherein in step (b), the series of relative horizontal shifts correspond to a defined range of relative rotation between the first and second iris images.

9. The ophthalmic laser system of claim 1, wherein for each of the first and second iris images, step (a1) includes identifying one or more occluders within the iris region, and step (a2) includes, for each horizontal line segment in a region of the rectangular image that corresponds to one of the one or more occluders, replacing pixel values of the rectangular image with values calculated by a one-dimensional linear interpolation using pixel values at two ends of the line segment.

10. The ophthalmic laser system of claim 9, wherein for each of the first and second iris images, the step of identifying occluders includes identifying eyelids, including:

down-sampling the iris image using a Laplacian pyramid, blurring the iris image using median blurring and then using Gaussian blurring in a vertical direction;

applying edge detection to the down-sampled and blurred iris image to detect horizontal edges to obtain an edge map;

masking detected edges outside of the limbus and inside the pupil;

applying morphology operations to the masked edge map to open it in the vertical direction and close it in a horizontal direction;

applying connected component analysis to the edge map to isolate and analyze individual connected components to identify connected components that correspond to the eyelids;

adding the limbus to the edge map; and constructing a mask from the edge map, by fitting a polyline to the center area of the image bound by the limbus and the connected components.

11. A method for treating a patient's eye, implemented in an ophthalmic laser system, the method comprising:

obtaining a measured astigmatism axis orientation of the eye, which has been measured while the patient is in an upright position;

obtaining a first iris image of the eye, which has been captured while the patient is in the upright position;

controlling a camera of the ophthalmic laser system to capture a second iris image of the eye while the patient is in a supine position;

computing a cyclotorsion rotation angle of the eye based on the first and second iris images of the eye, including:

(a) for each of the first and second iris images:

(a1) identifying an iris region of the iris image which corresponds to an iris of the eye between a pupil boundary and a limbus;

(a2) transforming the iris region into a rectangular image, wherein a radial coordinate in the iris image is mapped to a vertical coordinate of the rectangular image, and an angular coordinate in the iris image is mapped to a horizontal coordinate of the rectangular image, and wherein the pupil boundary and the limbus are respectively mapped to two horizontal edges of the rectangular image;

(a3) applying a horizontal one-dimensional band-pass filter to each horizontal line of the rectangular image to generate a transformed rectangular image; and (a4) binarizing each horizontal line of the transformed rectangular image to generate a binary rectangular image, whereby a first binary rectangular image and a second binary rectangular image having the same dimensions are generated from the first and second iris images, respectively;

(b) comparing the first and second binary rectangular images at a series of relative horizontal shifts to determine an optimum horizontal shift value that produces a highest similarity between the first and second binary rectangular images; and (c) computing the cyclotorsion rotation angle of the eye between the first and second iris images based on the optimum horizontal shift value; and while the patient is in the supine position, controlling a laser source and an optical delivery system of the ophthalmic laser system based on the measured astigmatism axis orientation and the computed cyclotorsion rotation angle to deliver a pulsed laser beam into the eye.

12. The method of claim 11, wherein for each of the first and second iris images, step (a2) includes tracing a plurality of rays from a pupil center, each ray intersecting the pupil boundary and the limbus at a first and a second point, respectively, and mapping a grayscale intensity profile of the iris image along each ray between the first and second points to a full vertical length of the rectangular image to form a column of the rectangular image.

13. The method of claim 12, wherein the mapping of the grayscale intensity profile from each of the plurality of rays to the full vertical length of the rectangular image is a linear mapping.

14. The method of claim 11, wherein the one-dimensional band-pass filter is a one-dimensional log-Gabor transform.

15. The method of claim 11, wherein for each of the first and second iris images, step (a4) includes, for each horizontal line of the transformed rectangular image:

calculating a mean of grayscale pixel values of the horizontal line; and binarizing each pixel of the horizontal line using the mean as a threshold.

16. The method of claim 11, wherein step (a4) includes, for each horizontal line of the transformed rectangular image:

calculating a mean of grayscale pixel values of the horizontal line; and binarizing each pixel of the horizontal line using two threshold values calculated from the mean, wherein pixels having grayscale pixel values between the two threshold values are masked; and wherein in step (b), pixels that are masked during the binarization step in either of the first or second binary rectangular images are disregarded in the comparison.

17. The method of claim 11, wherein step (b) includes, at each relative horizontal shift, computing a Hamming distance between first and second binary rectangular images as a measure of similarity.

18. The method of claim 11, wherein in step (b), the series of relative horizontal shifts correspond to a defined range of relative rotation between the first and second iris images.

19. The method of claim 1, wherein for each of the first and second iris images, step (a1) includes identifying one or more occluders within the iris region, and step (a2) includes, for each horizontal line segment in a region of the rectangular image that corresponds to one of the one or more occluders, replacing pixel values of the rectangular image with values calculated by a one-dimensional linear interpolation using pixel values at two ends of the line segment.

20. The method of claim 19, wherein for each of the first and second iris images, the step of identifying occluders includes identifying eyelids, including:

down-sampling the iris image using a Laplacian pyramid, blurring the iris image using median blurring and then using Gaussian blurring in a vertical direction;

applying edge detection to the down-sampled and blurred iris image to detect horizontal edges to obtain an edge map;

masking detected edges outside of the limbus and inside the pupil;

applying morphology operations to the masked edge map to open it in the vertical direction and close it in a horizontal direction;

applying connected component analysis to the edge map to isolate and analyze individual connected components to identify connected components that correspond to the eyelids;

adding the limbus to the edge map; and constructing a mask from the edge map, by fitting a polyline to the center area of the image bound by the limbus and the connected components.

* * * * *